United States Patent [19]

Køhnke

[11] Patent Number: 5,067,707
[45] Date of Patent: Nov. 26, 1991

[54] APPARATUS FOR RESPIRATORY TRAINING

[75] Inventor: Ole B. Køhnke, Hjortekrogen, Denmark

[73] Assignee: Ambu International A/S, Glostrup, Denmark

[21] Appl. No.: 435,445

[22] PCT Filed: Mar. 22, 1989

[86] PCT No.: PCT/DK89/00064
§ 371 Date: Nov. 22, 1989
§ 102(e) Date: Nov. 22, 1989

[87] PCT Pub. No.: WO89/09023
PCT Pub. Date: Oct. 5, 1989

[51] Int. Cl.⁵ .............................................. A63B 23/00
[52] U.S. Cl. ...................................... 272/99; 128/725
[58] Field of Search ........................... 272/99; 73/747; 128/725

[56] References Cited

U.S. PATENT DOCUMENTS

| 4,380,173 | 4/1983 | Wozniak | 73/747 |
| 4,533,137 | 8/1985 | Sonne | 272/99 |
| 4,739,987 | 4/1988 | Nicholson | 272/99 |

FOREIGN PATENT DOCUMENTS 1114650 10/1961 Fed. Rep. of Germany ........ 73/747

Primary Examiner—Stephen R. Crow
Attorney, Agent, or Firm—Watson, Cole, Grindle & Watson

[57] ABSTRACT

A respiratory training apparatus comprises a mouthpiece, a respiration chamber which includes an inspiration chamber having a check valve and an expiration chamber having a check valve. Exchangeable covers are provided for the chambers for varying the air flow resistance. A branch pipe comprising a valve is connected through as flexible tube to the lower end of a manometer's U-shaped tube, and a pipe stub extends from the mouthpiece and communicates with the upper end of one of the tube sections of the U-shaped manometer.

6 Claims, 2 Drawing Sheets

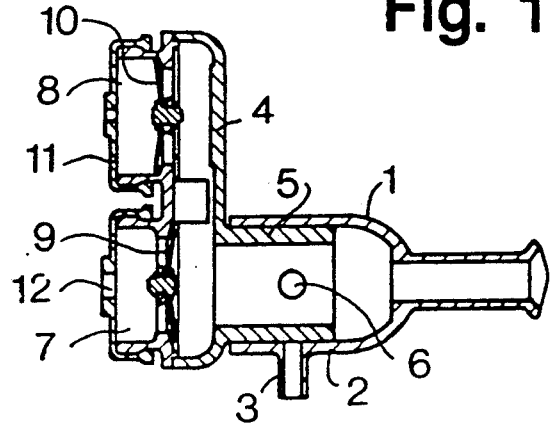
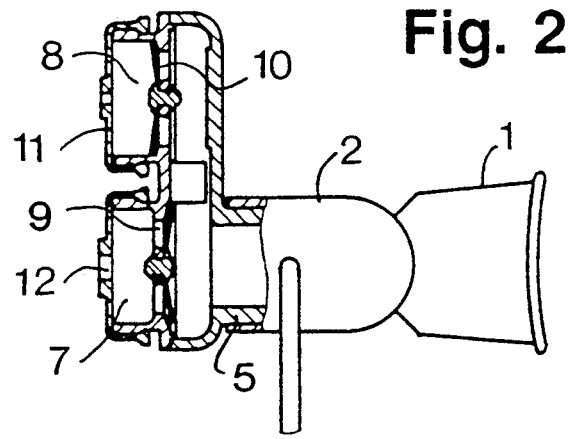
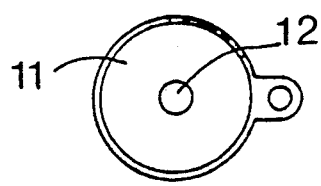
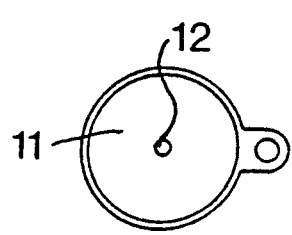

APPARATUS FOR RESPIRATORY TRAINING

BACKGROUND OF THE INVENTION

The present invention relates to an apparatus for respiratory training having a mouth piece and a respiration chamber coacting with the mouth piece, the respiration chamber having an inspiratory opening comprising a check valve which permits the inflow of inspiratory air and prevents the outflow of expiratory air, and an expiratory opening comprising a check valve which permits the outflow of expiratory air and prevents the inflow of inspiratory air, and exchangeable obstruction means for varying the resistance to the air flow through the inspiratory and expiratory openings.

It is known to increase the endurance of sick persons by systematical training of their respiratory musculature using a respiratory apparatus of the kind described above. In the use of such apparatus obstruction means are selected which are capable of creating a certain resistance to both inspiration and expiration during respiration, thus imparting increased exertion to the respiratory musculature.

While up to now considerable attention has been directed towards the training of the inspiratory musculature, the training of the expiratory musculature has been subject to relatively little interest, as the expiratory muscles do not have to perform active work until the physical performance and thus the requisite respiration exceed values which are not relevant for persons suffering from lung diseases.

Tests have shown that the respiratory training of persons in good health, e.g. athletes, should be carried out in such a way that the inspiratory low pressure reaches a value corresponding to about half the maximum inspiratory low pressure capacity of that person.

Owing to the risk of affecting the blood circulation it is vital that the resistance exerted by the respiratory apparatus to expiration does not exceed a certain value, viz. a value corresponding to an expiratory pressure of 10 cm water column. It is the object of the present invention to provide a training apparatus of the type described above to be used by persons in good health and which enables determination of the maximum inspiratory pressure capacity of such persons and ensures that the respiratory training takes place at an inspiratory pressure which is in a given ratio to the maximum inspiratory pressure, and at a given expiratory pressure.

It is a further object of the invention to provide a simple and readily transportable respiratory apparatus.

SUMMARY OF THE INVENTION

These and other objects, which will become apparent in the following, are achieved with the respiratory training apparatus of the invention, which apparatus is characterized in that it further comprises a branch-off stub extending from the mouth piece, and a manometer in the form of a substantially vertically suspended liquid-containing U-shaped tube, one top end of which may be connected to the branch-off stub on the mouth piece through a flexible tube, and the other top end of which is in communication with the atmosphere.

In order to determine the desired inspiratory low pressure and the desired expiratory pressure during the respiratory training, the respiration chamber is separated from the mouth piece, and the branch-off stub of the mouth piece is connected to the manometer through the flexible tube. The free end of the mouth piece is closed, and during inspiration a low pressure is established in the flexible tube between the mouth piece and the manometer. Thereby, the liquid level is raised in the tube portion which is in communication with the mouth piece and the liquid level in the other tube portion is correspondingly lowered. Conversely, during expiration a high pressure is established in the flexible tube connected to the manometer. Consequently, the liquid level in the other branch of the manometer will rise, and the positive expiratory pressure may be determined. If water is used as a manometer liquid, the water column height from the equilibrium state will indicate half of the high pressure/low pressure which is established in the mouth piece. By using a tube manometer provided with a scale between the two tube portions and spacing the scale unit marks 0.5 cm apart as from the equilibrium level, the scale will directly display the low/high pressures in cm water column.

Since the inspiratory low pressure capacity of a fit person may be as high as about 200 cm water column it may be necessary to use a manometer having a total length of about 220 cm.

This being inconvenient and since moreover, as mentioned above, it has been found that the respiratory training should preferably be carried out by inspiration up to a low pressure which constitutes a percentage, e.g. 50%, of the maximum inspiratory low pressure, the apparatus according to the invention preferably further comprises a pressure reducing valve which, when placed in the free end of the mouth piece, causes the low pressure in the branch-off opening to be, e.g., half the low pressure within the mouth piece proper.

When such a pressure reducing valve is used, the maximum liquid level indicated on the manometer scale thus corresponds to only half the maximum inspiratory low pressure, but that liquid level corresponds to the optimum inspiratory low pressure during respiratory training without use of a pressure reducing valve. The manometer scale is preferably provided with a settable indicator, and by setting of same at the liquid column height obtained in the determination of the maximum inspiratory low pressure using a pressure reducing valve, the liquid column height offering optimum training without the use of a pressure reducing valve is thus at the same time determined.

The above-mentioned obstruction means, which are preferably in the form of covers provided with a central hole whose diameter varies from cover to cover, and which may be placed across the inspiratory and expiratory openings, are preferably selected so as to provide the desired inspiratory and expiratory pressures when breathing is performed about 12 times per minute, each inspiration lasting about 2 seconds and each expiration lasting about 3 seconds.

The manometer preferably comprises a flexible plastic tube which, after discharge of liquid, may be bent and packed into a suitcase for the user to carry with him. The U-shaped tubular manometer is preferably connected at its lowermost end to a bifurcated tube provided with a valve. The bifurcated tube is used for filling and for adjustment of the liquid level in the manometer, e.g. by connecting a hypodermic syringe containing coloured water to the bifurcated tube prior to opening the valve. The two tube portions may then be filled without the risk of confining air bubbles therein when the syringe piston is advanced.

Similarly, the equilibrium state may be moved downwards by retracting the piston. Filling and setting of the manometer as well as discharge of liquid therefrom may thus be effected in a very simple and hygienic manner.

The two parallel tube portions of the manometer and one or more intermediary connecting walls onto which a scale may subsequently be printed or attached are preferably produced by extrusion of a transparent elastomeric material.

The mouth piece is preferably connected to the respiration chamber through a tubular member extending from the mouth piece which tubular member surrounds a corresponding tubular member extending from the respiration chamber.

The branch-off stub on the mouth piece is preferably located on the tubular member, and in the tubular member on the respiration chamber a corresponding opening is provided. Thus, it is rendered possible to establish/disestablish connection between the mouth piece and the manometer by turning the one member in relation to the other when the flexible tube is connected to the manometer.

When the mouth piece and respiration chamber are used exclusively for respiratory training the two members are also located in such a position relative to each other that inflow or outflow of air through the branch-off stub is prevented.

BRIEF DESCRIPTION OF THE DRAWINGS

The invention will now be described in further detail with reference to the accompanying drawing, wherein FIG. 1 is a sectional view of a mouth piece and a respiration chamber in communication therewith in its position for training, FIG. 2 is a partially sectional view of the mouth piece and the respiration chamber according to FIG. wherein the mouth piece is turned 90 in relation to the respiration chamber, FIGS. 3 and 4 are plane views of two covers to be attached to the respiration chamber.

DETAILED DESCRIPTION OF THE PREFERRED EMBODIMENTS

Figure 5:
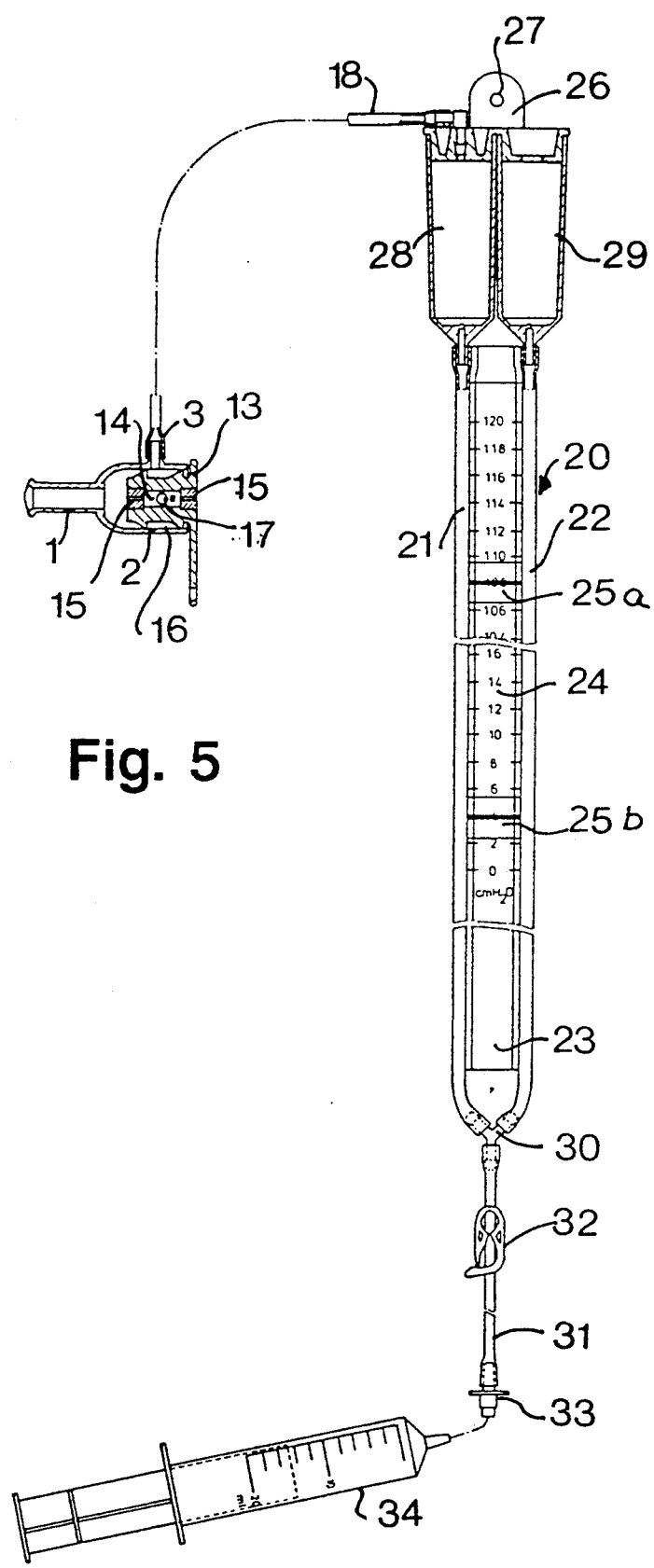
FIG. 5 is a sectional view of a mouth piece provided with a reducing valve and a plane view of a U-shaped tubular manometer and a syringe for filling the manometer with water.

The training apparatus shown in FIGS. 1 and 2 consists of a mouth piece 1 having a tubular member 2 provided with a branch-off stub 3 and a respiration chamber 4. The respiration chamber is connected to the tubular member 2 of the mouth piece 1 through a tubular member 5 in which a hole 6 is provided which, by turning the tubular member in relation to the other, may be brought into a position where the hole in the branch-off stub 3 may be in communication with the interior of the mouth piece through the hole 6 in the tubular member 5.

The respiration chamber 4 is provided with an inspiratory opening 7 and an expiratory opening 8 in which openings, valves 9 and 10, respectively, are provided. Each of the openings is covered by a snapped-on cover 11 having a central hole 12, the diameter of which varies from cover to cover, cf. FIGS. 3 and 4.

FIG. 5 shows a mouth piece 1 like the one shown in FIGS. 1 and 2, and in the tubular member 2 of the mouth piece a reducing valve 13 is inserted. The reducing valve has an internal space 14 which is in communication with the interior of the mouth piece, and with the ambient air, respectively, through nozzles 15. The reducing valve 13 is moreover provided with a peripheral recess 16 which is in communication with the space 14 through a hole 17. The peripheral recess 16 is in communication with the branch-off stub 3 and, through a flexible tube which is mounted thereon, with a U-shaped manometer generally designated 20.

The manometer 20 is composed of two plastic tubes 21 and 22 which are connected to each other by means of an intermediary wall 23 whereto a scale 24 is attached which comprises two displaceable indicators 25a, 25b.

At the one end of the manometer a suspension lug 26 is provided having a hole 27. At the same end of the manometer the tubes are connected to two buffer containers 28 and 29, the container 28 being connected in an airtight way to the tube 18 and the container 29 being in communication with the ambient air through a hole.

At its opposite end the manometer is in communication with a bifurcated tube 30 which may be connected through a further tube 31 on which a squeeze valve 32 is located, and through a mouth piece 33 to a syringe 34 for dispensing the liquid into the manometer.

When filling the manometer 20 with water from the syringe 34 the liquid level is adjusted so as to level with 0 on the scale 24.

In order to determine his maximum inspiratory pressure capacity the user puts the mouth piece shown in FIG. 5 into his mouth and takes the deepest breath possible. Hereby, the liquid level in the tube 21 rises, and it drops correspondingly in the tube 22. Using a reducing valve wherein the two passages are of identical diameters and lengths, the low pressure in the flexible tube becomes half the size of the low pressure in the mouth piece, and if a pressure of e.g. 50 cm water column is read off the scale the actual inspiratory low pressure is 100 cm water column. The indicator 25a is then set to the value read off the scale, and this value represents the optimum low pressure to be established for the training of the inspiratory musculature.

The reducing valve is then removed and the mouth piece 1 is connected to a respiration chamber the position of which in relation to the mouth piece is as indicated in FIG. 2.

By mounting different covers on the inspiratory opening it is now possible to select the cover which exerts suitable resistance to inspiration and at the same time ensures that the inspiratory low pressure only reaches a value corresponding to the setting of the indicator.

Thereafter a cover for the expiratory opening is selected which provides a maximum pressure of e.g. 5 cm water column.

The flexible tube may now be removed and the mouth piece may be turned in relation to the respiration chamber so as to occupy the position shown in FIG. 1, and the actual respiratory training may now begin.

I claim:
1. A portable apparatus for respiratory training comprising:
   (a) a mouthpiece,
   (b) a respiration chamber communicating with said mouthpiece and comprising:
      (i) a first opening comprising a one-way valve allowing inflow of inspiratory air and preventing outflow of expiratory air,

(ii) a second opening comprising a one-way valve allowing outflow of expiratory air and preventing inflow of inspiratory air,
(c) exchangeable obstruction means for varying the flow of air through he first and second openings,
(d) a manometer comprising a U-shaped flexible plastic tube for holding a liquid and a scale located between the two parallel tube sections of the manometer, said manometer having at its lowermost end a branch pipe for supplying liquid to and removing liquid from said manometer, said branch pipe comprising a valve, and
(e) a pipe stub extending from the mouthpiece and communicating with the upper end of one of the two tube sections, the upper end of the other tube section communicating with surrounding atmosphere.

2. An apparatus according to claim 1, wherein the scale comprises at least one settable indicator.

3. An apparatus according to claim 1, further comprising a pressure reduction valve for insertion into the mouthpiece.

4. An apparatus according to claim 1, wherein the two tube sections of the manometer are interconnected by a wall, and wherein the tube sections and the wall are made from an elastomeric material by extrusion.

5. An apparatus according to claim 1, wherein the mouthpiece comprises a tubular member adapted to be inserted on a tubular member extending from the respiration chamber.

6. Ann apparatus according to claim 5, wherein the pipe stub extending from the mouthpiece is provided on the tubular member of the mouthpiece and wherein a hole is provided in the wall of the tubular member of the respiration chamber, said hole being located in such a manner that it can be aligned with the interior of the pipe stub extending from the mouthpiece.

* * * * *